US009188685B2

United States Patent
Takayanagi et al.

(10) Patent No.: US 9,188,685 B2
(45) Date of Patent: Nov. 17, 2015

(54) CALIBRATION METHOD FOR RADIATION DETECTOR, AND PARTICLE THERAPY SYSTEM

(71) Applicant: HITACHI, LTD., Tokyo (JP)

(72) Inventors: Taisuke Takayanagi, Hitachi (JP);
Hideaki Nishiuchi, Hitachinaka (JP);
Masahiro Tadokoro, Hitachiota (JP);
Yusuke Fujii, Hitachi (JP); Takeji Sakae, Tsukuba (JP); Toshiyuki Terunuma, Tsukuba (JP)

(73) Assignee: HITACHI, LTD., Tokyo (JP)

( * ) Notice: Subject to any disclaimer, the term of this patent is extended or adjusted under 35 U.S.C. 154(b) by 334 days.

(21) Appl. No.: 13/776,002

(22) Filed: Feb. 25, 2013

(65) Prior Publication Data

US 2013/0221213 A1    Aug. 29, 2013

(30) Foreign Application Priority Data

Feb. 29, 2012   (JP) .................................. 2012-043532

(51) Int. Cl.
*G01T 7/00*   (2006.01)
*A61N 5/10*   (2006.01)
*G01T 1/29*   (2006.01)

(52) U.S. Cl.
CPC .............. *G01T 7/005* (2013.01); *A61N 5/1048* (2013.01); *A61N 5/1075* (2013.01); *G01T 1/29* (2013.01); *A61N 2005/1087* (2013.01)

(58) Field of Classification Search
CPC ................................... G01T 7/00; G01T 7/005
See application file for complete search history.

(56) References Cited

U.S. PATENT DOCUMENTS

2011/0231147 A1   9/2011   Takayanagi et al.

FOREIGN PATENT DOCUMENTS

JP      2011-153833 A     8/2011

OTHER PUBLICATIONS

Nichiporov et al, "Multichannel detectors for profile measurement in clinical proton fields," 2007, Med. Phys. 34(7) Jul. 2007, pp. 2683-2690.*
Yajima et al ("Development of a multi-layer ionization chamber for heavy-ion radiotherapy," 2009, Institute of Physics and Engineering in Medicine, pp. N107-N114.*

(Continued)

*Primary Examiner* — Constantine Hannaher
*Assistant Examiner* — Faye Boosalis
(74) *Attorney, Agent, or Firm* — Mattingly & Malur, PC (57) ABSTRACT

A stacked type of radiation detector and a calibration method that enables the radiation detector to correct variations in sensor-specific output easily and within a short time, without using a water-phantom dose detector. The radiation detector is equipped with a sensor section including a plurality of sensors arranged in layers in a traveling direction of a particle beam. A dummy absorber has water-equivalent thickness equal to an average water-equivalent thickness of the sensors. A signal-processing unit calculates sensor-specific calibration coefficients using a measurement result obtained during irradiation of the radiation detector with the radiation when electrical signals developed in each sensor are measured, and a measurement result obtained during irradiation of the radiation detector with the radiation when the sensor section is moved in the traveling direction of the radiation, then the dummy absorber is set in place, and electrical signals developed in each sensor are measured.

20 Claims, 7 Drawing Sheets

(56) References Cited

OTHER PUBLICATIONS

Shimbo, M. et. al.; "Development of a Multi-layer Ion Chamber for Measurement of Depth Dose Distributions of Heavy-ion Therapeutic Beam for Individual Patients"; Nippon Acta Radiologica; 2000; vol. 60; pp. 274-279.

Yajima, K. et al.; "Development of a multi-layer ionization chamber for heavy-ion radiotherapy"; Physics in Medicine and Biology; 2009; vol. 54; pp. N107-N114.

Nichiporov, D. et al; "Multichannel detectors for profile measurements in clinical proton fields"; Med. Phys.; Jul. 2007; vol. 34; No. 7; pp. 2683-2690.

Brusasco C. et al; "A dosimetry system for fast measurement of 3D depth-dose profiles in charged-particle tumor therapy with scanning techniques"; Nuclear Instruments and Methods in Physics Research B 168; 2000; pp. 578-582.

* cited by examiner

CALIBRATION METHOD FOR RADIATION DETECTOR, AND PARTICLE THERAPY SYSTEM

BACKGROUND OF THE INVENTION

1. Field of the Invention

The present invention relates to a method for calibrating a radiation detector, and to a particle therapy system.

2. Description of the Related Art

A scanning method is becoming widespread in particle therapy. The scanning method is a technique used to divide a target region into very small segments, called spots, and irradiate each spot independently with a narrow beam having a small diameter of $1\sigma=3$ to 20 mm. The irradiation is stopped once a predetermined dose has been delivered to the spot, and after that, a next spot is scanned with the same beam. Scanning magnets are used when the beam is to be scanned in a direction perpendicular to a direction in which the beam travels (hereinafter, this scanning direction is referred to as the lateral direction, and likewise the traveling direction of the beam, as the depth direction). After the predetermined dose has been delivered to a certain depth in all spots, the beam is scanned in the depth direction. In this case, energy of the beam is changed using an accelerator or a range shifter. Finally, a uniform dose is delivered to all spots, that is, the entire target.

During these scans, an operator of the particle therapy system measures the scan positions, Bragg curve profiles, and dose distribution patterns of the beams, analyzes measurement results, and judges whether the system is correctly adjusted.

Traditionally known radiation detectors are constructed to include a plurality of parallel-plate ionization chambers formed in stacked form in the depth direction, and to be able to measure depth dose distributions of particle beams at one time, and examples of these devices are described in JP-2011-153833-A and M. Shimbo, et. al., "Development of a Multilayer Ion Chamber for Measurement of Depth Dose Distributions of Heavy-ion Therapeutic Beam for Individual Patients", NIPPON ACTA RADIOLOGICA 2000 60 274-279.

Each of the stacked ionization chambers usually varies in dimensions and in performance characteristics, and even if the target is scanned with beams equal in the number of particles and in energy level, results output from a signal-processing unit will usually differ for each ionization chamber. This is because thickness of the ionization chamber in the depth direction varies from chamber to chamber, and because conversion from an electric charge into a digital value in the signal-processing unit tends to vary in efficiency. For example, a 10% variation in the thickness of the ionization chamber appears as a 10% variation in the charge output. These variations are due to machining errors, and are therefore difficult to avoid. Traditionally, these variations have been calibrated by comparison with measurement results output from a water-phantom dose detector.

SUMMARY OF THE INVENTION

However, using a water-phantom dose detector to calibrate each stacked ionization chamber has required a great deal of labor and time.

An object of the present invention is to provide: a calibration method for a stacked type of radiation detector, this calibration method enabling variations in sensor-specific output to be corrected within a short time and easily, without using a water-phantom dose detector; and a particle therapy system used with the radiation detector employing the calibration method.

In order to attain the above object, a radiation detector that the present invention provides as an aspect thereof, includes a sensor section having radiation sensors stacked one another; a dummy absorber with water-equivalent thickness equal to average water-equivalent thickness of the stacked radiation sensors; a dummy absorber driving control section configured to place the dummy absorber at an anterior position in a direction of measurement by the sensor section, with the anterior position corresponding to a position at the line where radiation propagates; a sensor section driving control device configured to move the sensor section through a distance equal to average thickness of the stacked radiation sensors, at the line where the radiation propagates; and a signal-processing unit for calculating calibration coefficients for each radiation sensor, from measurement results output from the radiation detector when the dummy absorber is placed at the anterior position, measurement results output from the radiation detector when the dummy absorber is not placed at the anterior position, and an integrated extraction dose value of the radiation extracted during acquisition of the two sets of measurement results.

The present invention enables a stacked type of radiation detector to correct variations in sensor-specific output easily and within a short time, without using a water-phantom dose detector.

DESCRIPTION OF THE PREFERRED EMBODIMENTS

Particle therapy systems that employ the scanning method are adjusted to within scan position errors of ±1 mm so that the system scans a beam laterally across an indicated position. These systems are also adjusted to within beam range errors of ±1 mm to ensure that the beam reaches an indicated depth level. The range denotes a maximum depth that the beam can reach when it travels through the medium, and this value depends upon incident energy of the beam.

To confirm adjustment results on the particle therapy system, a radiation detector measures the scanning position and Bragg curve of the beam. The Bragg curve is a distribution of linear energy transfer (LET) in the depth direction, expressed in terms of [J/m], and depends upon the incident energy of the beam. More specifically, LET is the energy that the particle beam passing through the medium transfers thereto while traveling through a unit distance in the depth direction. The beam's reachable depth is calculated from the Bragg curve. A lateral dose distribution and a dose distribution in the depth direction are also measured during volumetric irradiation. The volumetric irradiation refers to forming a uniform dose distribution over a given region (called a target region) of the object or subject in accordance with a predetermined scanning sequence.

The radiation detector consists mainly of a radiation sensor, which reacts to the radiation and outputs an electrical signal, and a signal-processing unit. A typical radiation sensor is an ionization chamber. The ionization chamber has a structure with an ionized layer (formed from air, a noble gas, or the like) that is interposed between two electrodes. The ionization chamber generates an electric field in the ionized layer by applying a high voltage to one electrode, and then collects an ionization charge that has been developed in the ionized layer during beam scanning. The quantity of ionization charge varies in proportional to an energy loss [MeV] of the beam in the ionized layer. In addition, the energy loss varies in proportional to a dose present at a placement location of the ionization chamber. The signal-processing unit converts into a digital value the charge that was developed in the ionized layer, and displays the digital value on a device such as a display. The signal-processing unit additionally stores the value into a recording unit such as a hard-disk drive.

A radiation detector with a plurality of parallel-plate ionization chambers built in stacked form in the depth direction is termed a stacked ionization chamber. The parallel-plate ionization chambers have construction with an ionized layer interposed in parallel between two electrodes of a plate-like shape. After being obtained from the ionized layer, an electric charge in coulombs [C] is multiplied by a conversion coefficient, to derive a dose in water, D, expressed in J/kg. The dose D is a value averaged by a water-equivalent volume of the ionized layer. The water-equivalent volume of the ionized layer is expressed in terms of [lateral area S]×[water-equivalent thickness in the depth direction] of the ionized layer. Water-equivalent thickness of a substance refers to thickness of the water used to impart to a particle beam an energy loss equal to an energy of the particle beam passed through the substance. For neutral particle rays, the water-equivalent thickness of a substance refers to thickness of the water used to reduce the number of particles that is equal to that of particle rays passed through the substance. The dose D that the particles having a charge impart to the substance satisfies a relationship of $D = LET \times n/\rho/S$, where "n" is the number of particles incident upon the ionized layer, and "$\rho$" is a density ($kg/m^3$) of the medium.

A water-phantom dose detector is a radiation detector with a compact radiation sensor placed in a water tank. The radiation sensor can be motor-driven to freely move in the water tank. A stacked ionization chamber calibration method utilizing this characteristic would use the following procedure. First, the water-phantom dose detector is irradiated with a beam under optional conditions, and while the radiation sensor is being scanned, a depth dose distribution is measured, one point at a time. Next, a stacked ionization chamber is irradiated with a beam under the same conditions as above, and a depth dose distribution is likewise measured. Finally, measurement results by the water-phantom dose detector and those of the stacked ionization chamber are compared and calibration coefficients are defined for each parallel-plate ionization chamber so that the two sets of measurement results match.

To use the water-phantom dose detector, it is necessary first to fill the water tank with water. Since this filling operation requires care so as not to cause damage to a therapy system due to spilled water, it takes a time of about tens of minutes to fill the tank. Filled water tank is very heavy, requiring careful handling. To ensure safety for an operator and avoid damaging the therapy system, an enough number of personnel should be involved in movement and position adjustment of the water-phantom dose detector and these operations must be performed as carefully as possible. The same also applies to tidying up the worksite after the measurement. Furthermore, the dose distribution measurement with the water-phantom dose detector is a time-consuming task, for it is necessary to scan the radiation sensor and measure distributions, one point at a time. The above method of using a water phantom to construct the ionization chambers constituting a stacked ionization chamber is therefore estimated to require troublesome preparatory steps and time-consuming calibration. Accordingly, the present invention provides a radiation detector calibration method and radiation detector designed so as to enable relatively rapid calibration without using a water phantom.

Hereunder, a configuration and operation of a radiation detector according to an embodiment of the present invention will be described using FIGS. 1 to 7.

First, an overall configuration including the radiation detector according to the present embodiment and a particle therapy system thereof is described below using FIG. 1.

Figure 1:
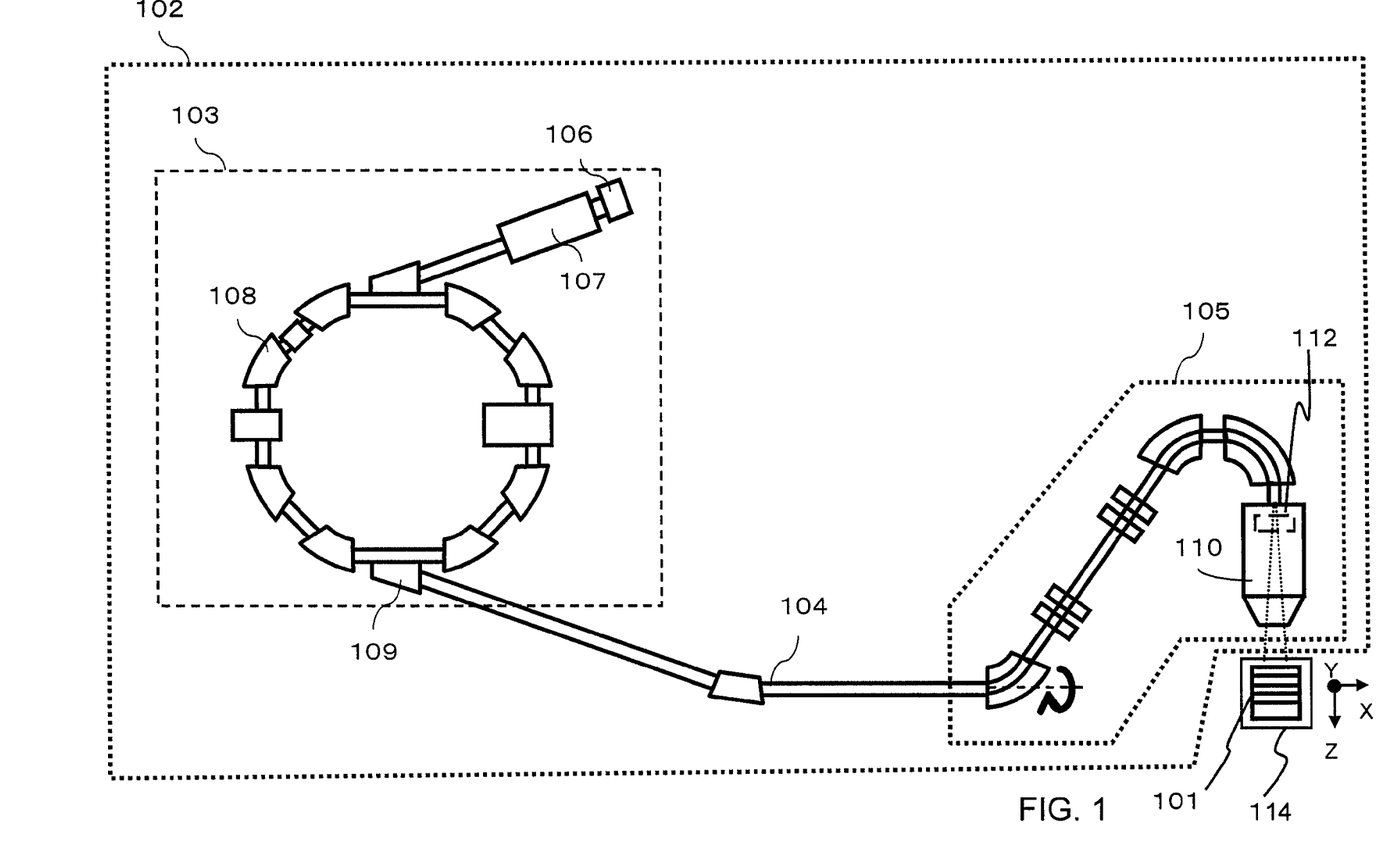
FIG. 1 is a block diagram showing an overall configuration of a radiation detector and particle therapy system according to an embodiment of the present invention.

FIG. 1 is a block diagram showing the overall configuration of the radiation detector and particle therapy system according to the embodiment of the present invention.

The particle therapy system includes a proton beam irradiation system 102 and a radiation detector 101. To conduct adjustment and performance evaluation of the proton beam irradiation system 102 which uses a scanning method, the radiation detector 101 measures a Bragg curve of a beam emitted from the proton beam irradiation system 102.

While the proton beam irradiation system 102 is herein described as an example of a beam irradiation apparatus, the present invention may instead be applied to a heavy-particle beam irradiation apparatus that uses carbon rays or other particle beams heavier than proton beams in mass. The invention can also be applied to a beam irradiation apparatus that uses photon beams, electron beams, muon($\mu$)-beams, pi($\pi$)-meson beams, or neutron beams. In addition, the proton beam irradiation system does not always need to be limited to a scheme based on scanning irradiation; it may be of a scheme based on scattering irradiation described later herein.

As shown in FIG. 1, the proton beam irradiation system 102 includes a proton beam generator 103, a proton beam transfer 104, and a rotating irradiation system 105. In the present embodiment, the rotating irradiation system 105 with a rotating gantry is described by way of example below, but the irradiation system may be of a fixed type.

The proton beam generator 103 includes an ion source 106, a preaccelerator 107 (e.g., a linear accelerator), and a synchrotron 108. Protons that have been generated by the ion source 106 are first accelerated by the preaccelerator 107. A proton beam that has extracted from the preaccelerator 107 is further accelerated to a predetermined energy level by the synchrotron 108 and then extracted from an extraction deflector 109 into the proton beam transfer 104. Finally, the proton beam (hereinafter, referred to simply as the beam) is used to irradiate the radiation detector 101 through the rotating irradiation system 105. The rotating irradiation system 105 includes a rotating gantry (not shown) and an irradiation nozzle 110. The irradiation nozzle 110, installed in the rotating gantry, rotates with the gantry. Part of the proton beam transfer 104 is also mounted in the rotating gantry. Although the synchrotron 108 is employed as a proton beam accelerator in the present embodiment, the proton beam accelerator can instead be a cychrotron or a linear accelerator.

Next, a scanning method that the irradiation nozzle 110 implements in the present embodiment is outlined below. In the scanning method, a region to be irradiated is divided into very small segments, called spots, and each of the spots is irradiated with a beam independently. The irradiation is stopped once a predetermined dose has been delivered to the spot, and after that, a next predetermined spot is scanned with the same beam. Two pairs of scanning magnets (not shown) that are mounted in the irradiation nozzle 110 are used when the beam is to be scanned in a lateral direction. After the predetermined dose has been delivered to a certain depth in all spots, the irradiation nozzle 110 scans the beam in a depth direction. The beam scan in the depth direction is implemented by changing the beam's energy using the synchrotron 108 or a range shifter (not shown) that is mounted in the irradiation nozzle 110 or the like. These processes are repeated until a uniform dose distribution is formed. The irradiation nozzle 110 is further equipped with a dose monitor 112 to detect an extraction (irradiation) dose of the beam.

A straight line through which a central portion of the beam passes under an unenergized state of the scanning magnets is defined as a beam axis in the present embodiment. In addition, a point at which the beam axis intersects with a rotational axis of the rotating irradiation system 105 is defined as an isocenter. In the scanning method, a lateral spread of the beam in a neighborhood of the isocenter is expressed as $1\sigma=3$ mm to 20 mm.

The radiation detector 101 is placed on a patient couch 114. The patient couch 114 can move the radiation detector 101 in a direction of the beam axis (this direction is called a Z-axis direction). The patient couch 114 can also move the radiation detector 101 in biaxial directions (X-axis direction and Y-axis direction) that are orthogonal to the Z-axis direction.

Next, a detailed configuration of the radiation detector 101 is described below using FIG. 2.

Figure 2:
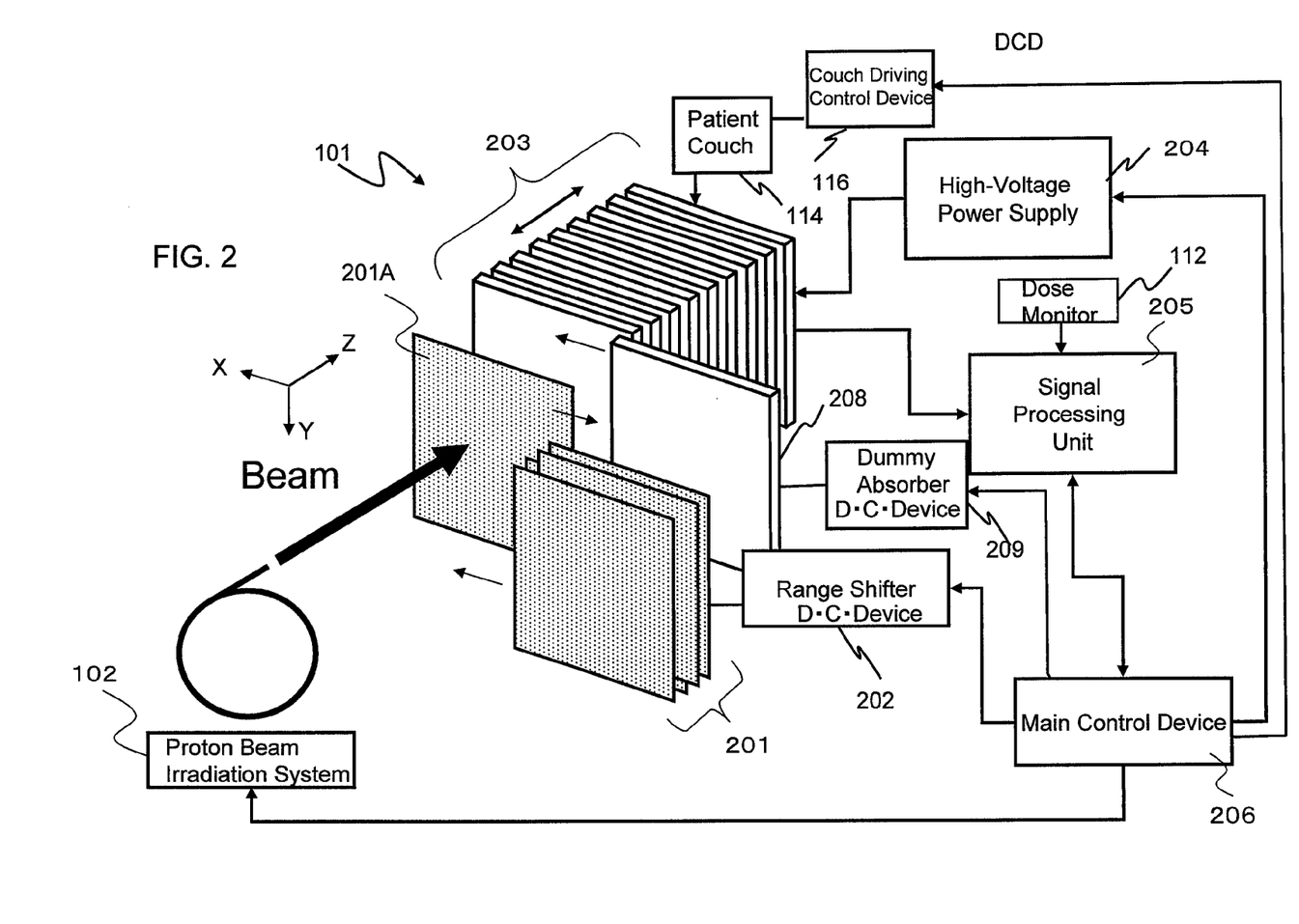
FIG. 2 is a block diagram showing a configuration of the radiation detector according to the embodiment of the present invention.

FIG. 2 is a block diagram showing the detailed configuration of the radiation detector according to the embodiment of the present invention. The same reference number or symbol as in FIG. 1 denotes the same detector element.

The radiation detector 101 shown in FIG. 1 includes a range shifter 201, a range shifter driving control device 202, a sensor section 203, a high-voltage power supply 204, a signal-processing unit 205, a main control device 206, a dummy absorber 208, and a dummy absorber driving control device 209.

The patient couch 114, also shown in FIG. 1, is controlled by a couch driving control device 116 to move the sensor section 203 in the direction of the Z-axis, the driving control device 116 also serving as a driving control device for the sensor section 203. A dose of the beam that has been detected by the dose monitor 112 shown in FIG. 1 is collected into the signal-processing unit 205. The driving control device for the sensor section 203 may be provided separately from the couch driving control device. In this case, the sensor section 203 would be movable by placing the radiation detector 101 on a cart, mobile carriage, or movable tabletop that can be moved on the couch.

The range shifter 201 is positioned upstream of the sensor section 203, in the traveling direction of the beam (hereinafter, this direction is referred to as the depth direction, that is, the direction of the Z-axis), and includes a plurality of energy absorbers 201A each different in water-equivalent thickness. To be more specific, five energy absorbers 201A exist and the water-equivalent thicknesses of these absorbers are 0.2 mm, 0.4 mm, 0.8 mm, 1.6 mm, and 3.2 mm. Upon the range shifter driving control device 202 sending a signal to the range shifter 201, the range shifter 201 operates a motor (not shown) and loads/unloads each energy absorber 201A onto/from a position through which the beam passes. After the beam has passed through the energy absorber 201A, the radiation detector 101 changes a measuring position through the water-equivalent thickness of that energy absorber, in the depth direction. In this way, the radiation detector 101 of the present embodiment controls the measuring position in the depth direction. Since useable water-equivalent thicknesses are in a thickness range creatable by combining a maximum of the five energy absorbers, a controllable position range is from 0.2 mm to 6.2 mm, inclusive, in units of 0.2 mm. The number, water-equivalent thicknesses, and material of energy absorbers 201A are arbitrary. The energy absorbers 201A in the present embodiment are plates formed from acrylonitrile butadiene styrene (ABS).

Next, a configuration of the sensor section 203 used for the radiation detector 101 of the particle therapy system according to the present embodiment is described below using FIG. 3.

Figure 3:
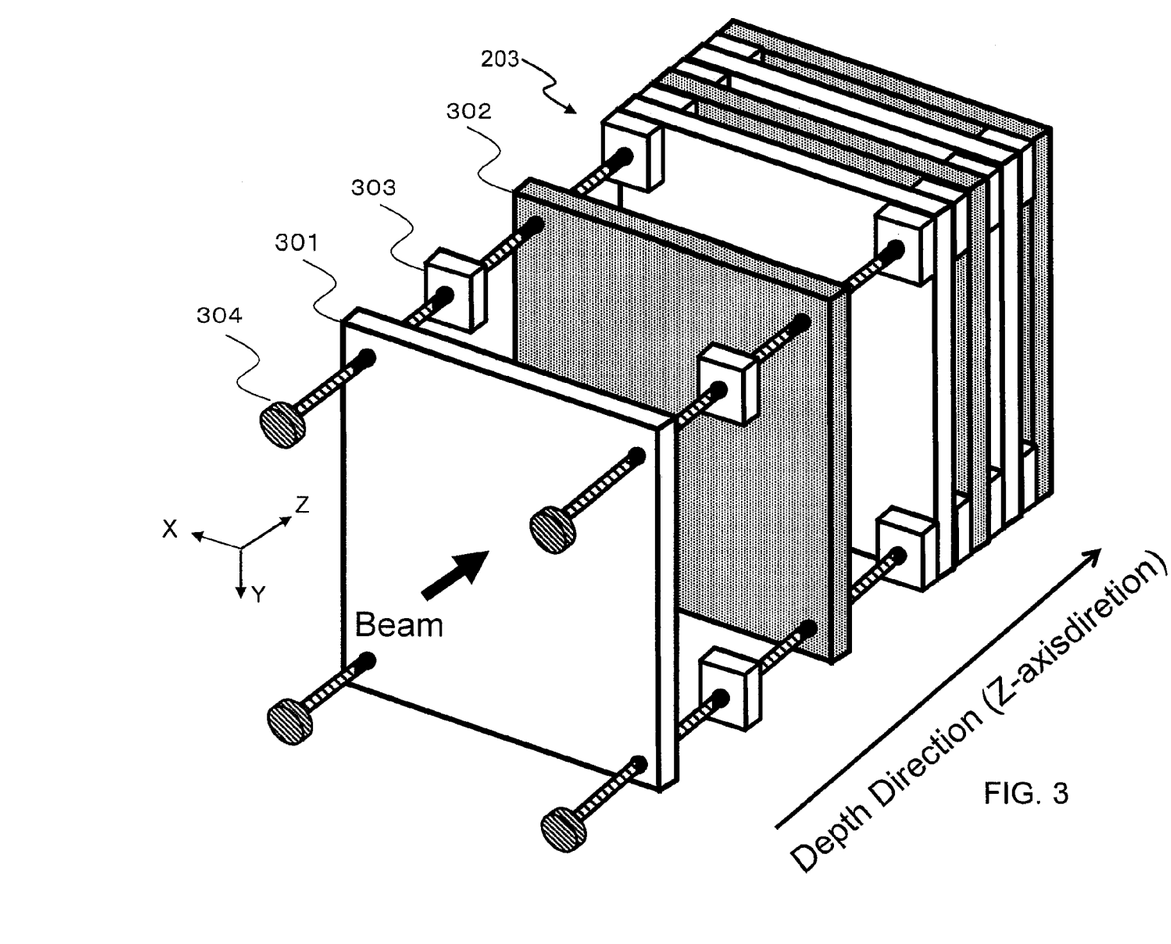
FIG. 3 is a perspective view showing a configuration of a sensor section used for the radiation detector according to the embodiment of the present invention.

FIG. 3 is a perspective view showing the configuration of the sensor section used for the radiation detector of the particle therapy system according to the embodiment of the present invention. The same reference number or symbol as in FIG. 2 denotes the same constituent element of the sensor section.

As shown in FIG. 3, the sensor section 203 includes printed circuit boards 301, each for collecting electric charges, and printed circuit boards 302, each for applying a high voltage, the two kinds of printed circuit boards being arranged in layers at alternate positions in the depth direction, the direction of the Z-axis. The number of layers constituting the printed circuit boards 301 and 302 is arbitrary, but at least one layer is required for each kind of board. In addition, the printed circuit boards 301 for electric-charge collection and the printed circuit boards 302 for high-voltage application both consist of three layers in the example of FIG. 3, but an actual number of layers is 50 for each kind of board.

A spacer 303 is inserted between one printed circuit board 301 and one printed circuit board 302. The insertion of the spacer 303 forms an ionized layer between the printed circuit board 301 and the printed circuit board 302. The spacer 303 is an electrical insulator. In this present embodiment, if the two kinds of printed circuit boards both consist of 51 layers, a total of 100 ionized layers will be formed. Each ionized layer is filled with a gas. In the present embodiment, the ionized layer is open to the atmosphere, and air is used as the ionizing gas. The ionized layer may be hermetically sealed and an alternative ionizing gas such as argon may be circulated using a gas pump.

The stacked printed circuit board section 301 for electric-charge collection, the stacked printed circuit board section 302 for high-voltage application, and the spacers 303 are each fixed using bolts 304. This fixing method, however, may be replaced by any other appropriate method enabling each printed circuit board 301, printed circuit board 302, and spacer 303 to be stably layered and fixed.

The printed circuit board 301 for electric-charge collection and the printed circuit board 302 for high-voltage application are glass epoxy sheets each having electrodes deposited on both sides of an X-Y plane orthogonal to the depth direction. The electrodes are made of copper and plated with nickel and gold. If the circuit board is an insulator, however, the kind of board is not limited to a glass epoxy. Likewise, if the electrode is an electric conductor, the kinds of materials used to form it will not always be copper, nickel, and gold. The present embodiment assumes that the printed circuit board 301 for electric-charge collection and the printed circuit board 302 for high-voltage application are substantially of the same thickness, and that both circuit boards have a water-equivalent thickness of 4.0 mm.

Next, a configuration of the printed circuit board 301 for electric-charge collection, used for the sensor section 203 in the radiation detector 101 of the present embodiment, is described below using FIG. 4.

Figure 4:
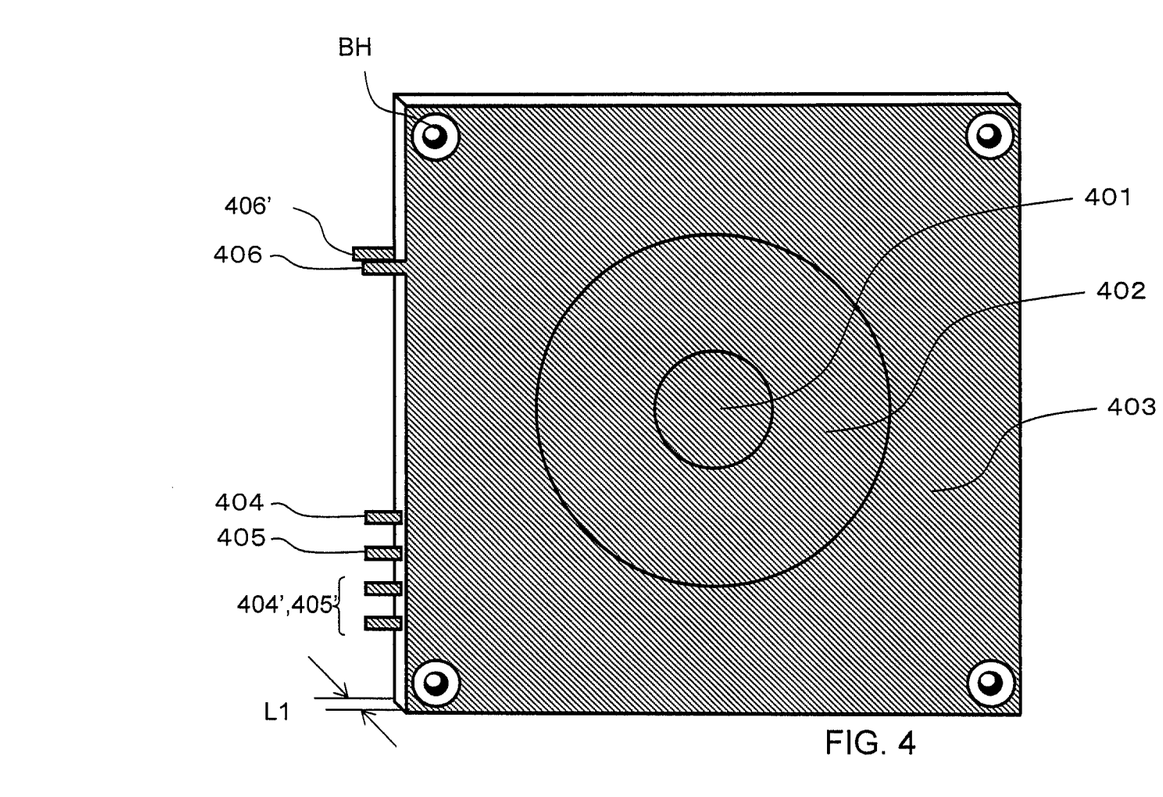
FIG. 4 is a perspective view showing a configuration of a printed circuit board used for electric-charge collection in the sensor section of the radiation detector according to the embodiment of the present invention.

FIG. 4 is a perspective view showing the configuration of the printed circuit board for electric-charge collection, used in the sensor section of the radiation detector according to the embodiment of the present invention. The same reference number or symbol as in FIG. 3 denotes the same constituent element of the printed circuit board.

As shown in FIG. 4, the electrodes on both sides (upper and lower surfaces) of the printed circuit board 301 for electric-charge collection are electrically divided into three regions. That is to say, a central region including a central part of the printed circuit board 301 is formed as a small electrode (first electrode) 401, a region surrounding the small electrode 401 is formed as a large electrode (second electrode) 402, and the outermost region is formed as a guard electrode (third electrode) 403. The small electrode 401 connects to one end of a lead wire 404, the large electrode 402 connects to one end of a lead wire 405, and the guard electrode 403 connects to one end of a lead wire 406. The lead wire 404 connecting to the small electrode 401, and the lead wire 405 connecting to the large electrode 402, further connect at the other ends of each to an input side of the signal-processing unit 205 through an internal layer of the board. This means that the lead wire 404 interconnects the small electrode 401 and the signal-processing unit 205 and that the lead wire 405 interconnects the large electrode 402 and the signal-processing unit 205. The other end of the lead wire 406 connecting to the guard electrode 403 is electrically grounded. The guard electrode 403 prevents current from leaking from the printed circuit board 302 for high-voltage application, to the small electrode 401 and the large electrode 402. The electrode region that the small electrode 401 and the large electrode 402 constitute is of a sufficiently larger shape than a beam spread out laterally in a two-dimensional Gaussian distribution form (with a spread of 1σ=3 mm to 20 mm in the neighborhood of the isocenter) when the beam is scattered and drifted in the radiation detector 101.

The electrodes of the printed circuit board 301 for electric-charge collection are of symmetric construction on both surfaces of the board. This board collects charges from the ionized layer facing the lower surface of the board as well as from the upper surface thereof. A lead wire 406', connected at one end thereof to the guard electrode on the lower surface, is electrically grounded at the other end of the lead wire. A lead wire 404' is connected at one end thereof to the small electrode on the lower surface, a lead wire 405' is connected at one end thereof to the large electrode on the lower surface, and the lead wires 404' and 405' are connected at the other ends of each to the signal-processing unit 205.

A bolt hole BH through which to pass one of the bolts 304 shown in FIG. 3 is formed at each of four corners of the printed circuit board 301 for electric-charge collection.

Next, a configuration of the printed circuit board 302 for high-voltage application, used for the sensor section 203 in the radiation detector 101 of the present embodiment, is described below using FIG. 5.

Figure 5:
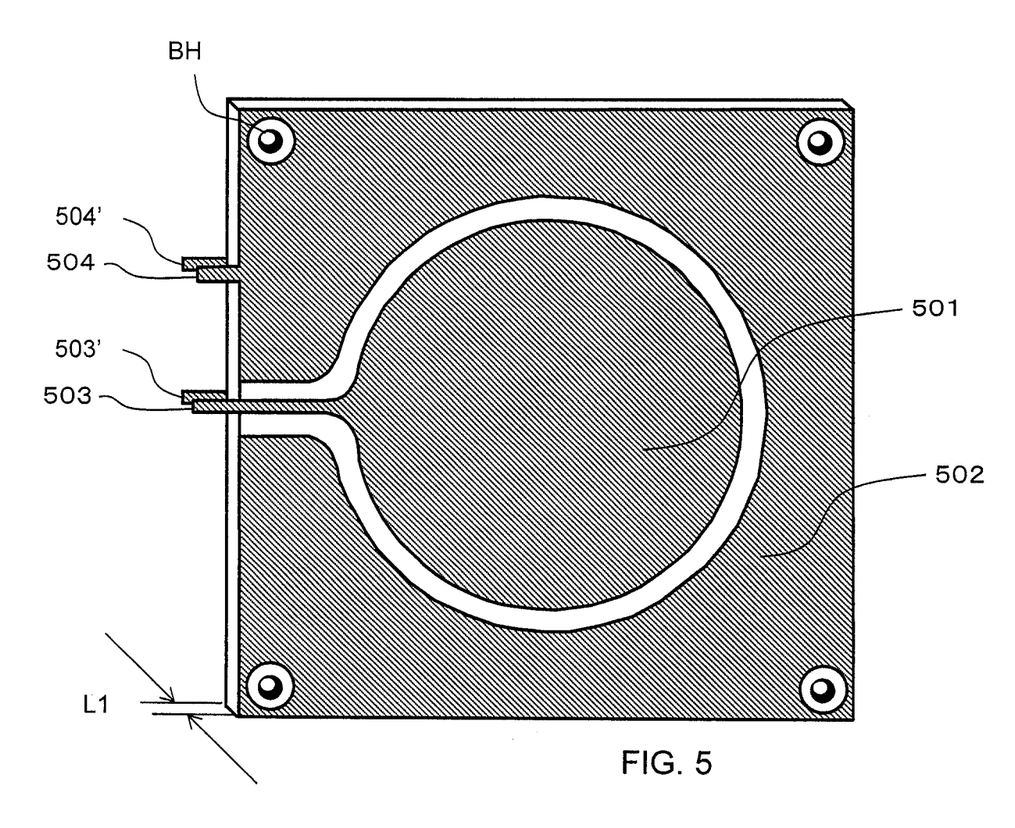
FIG. 5 is a perspective view showing a configuration of a printed circuit board used for high-voltage application in the sensor section of the radiation detector according to the embodiment of the present invention.

FIG. 5 is a perspective view showing the configuration of the printed circuit board for high-voltage application, used in the sensor section of the radiation detector according to the embodiment of the present invention. It is to be noted that the same reference number or symbol as in FIG. 3 denotes the same constituent element of the printed circuit board.

As shown in FIG. 5, the electrodes of the printed circuit board 302 for high-voltage application are electrically divided into two regions. That is to say, a central region of the printed circuit board 302 is formed as a high-voltage application electrode 501, and an outer region thereof is formed as a guard electrode 502. The high-voltage application electrode 501 connects to one end of a lead wire 503, and the guard electrode 502 connects to one end of a lead wire 504. The lead wire 503 interconnects the high-voltage application electrode 501 and the high-voltage power supply 204, and applies a high voltage (up to several thousands of volts in absolute value) from the high-voltage power supply 204 to the high-voltage application electrode 501. The lead wire 504 connecting to the guard electrode 502 is electrically grounded at one end of the lead wire. The guard electrode 502 prevents current from leaking from the printed circuit board 302 for high-voltage application, to the small electrode 401 and large electrode 402 of the printed circuit board 301 for electric-charge collection. Since a voltage of nearly 0 V is applied between the small electrode 401 and large electrode 402 of the printed circuit board 301, an electric field is developed in the depth direction of an ionized layer.

The electrodes of the printed circuit board 302 for high-voltage application are of symmetric construction on both surfaces of the board. This board applies the high voltage to the high-voltage application electrode on the lower surface of the board as well as to the high-voltage application electrode on the upper surface thereof. A lead wire 504', connected at one end thereof to the guard electrode on the lower surface, is electrically grounded at the other end of the lead wire. A lead wire 503' is connected at one end thereof to the high-voltage application electrode on the lower surface, and connected at the other end to the high-voltage power supply 204.

A bolt hole BH through which to pass one of the bolts 304 shown in FIG. 3 is formed at each of four corners of the printed circuit board 302 for high-voltage application.

The printed circuit board 301 for electric-charge collection has been described above as having a double-concentric electrode shape in the present embodiment. However, the electrode shape is arbitrary. For example, to form a lateral dose distribution pattern, the electrodes may be divided into a pixel or strip shape for independent acquisition of ionization charge from each of multiple segments. If a desired electric field distribution can be formed in the ionized layer, the electrode shape of the printed circuit board 302 for high-voltage application is also arbitrary.

Since the sensor section 203 has the above construction, a portion from the center of the printed circuit board 301 to that of the adjacent printed circuit board 302 in the depth direction operates as one sensor. Additionally in the present embodiment, as described above, the printed circuit board 301 for electric-charge collection and the printed circuit board 302 for high-voltage application are substantially of the same thickness, and both have a water-equivalent thickness of 4.0 mm on the average. An energy loss of the beam in the ionized layer can be ignored, so each sensor also has an average water-equivalent thickness of 4.0 mm.

Actual thicknesses of the printed circuit board 301 and the printed circuit board 302 are both about 2.0 mm. A space, which can be a ionized layer, between the printed circuit board 301 and the printed circuit board 302 is 2.0 mm thick. Each sensor itself in the present embodiment, therefore, is likewise 4.0 mm thick on the average. The thickness of the sensor itself and the water-equivalent thickness thereof do not need to be the same.

Since the water-equivalent thicknesses of each sensor are 4.0 mm on the average, if the range shifter 201 is not used, the radiation detector 101 of the present embodiment can measure Bragg curve data at intervals of 4.0 mm.

Referring again to FIG. 2, the signal-processing unit 205 independently integrates for each sensor the ionization charge that the small electrodes and large electrodes of each layer of the sensor section 203 have acquired. The signal-processing unit 205 likewise integrates ionization charge that has been output from the dose monitor (not shown). The dose monitor 112 is provided at the passing position of the beam in the irradiation nozzle 110 in order to monitor irradiation doses of the beam in each spot. The dose monitor 112 is a parallel-plate ionization chamber, which outputs ionization charges proportional to energy losses of the beam in the ionized layer, to the signal-processing unit 205. Finally, the signal-processing unit 205 digitizes integration results on these ionization charges, and transmits the digitized results to the main control device 206. The main control device 206 standardizes the integrated value that has been obtained from the sensor section 203, by using the integrated value that has been obtained from the dose monitor, and thereby corrects any variations in measurement results due to changes in beam irradiation dose.

As in the present embodiment, a radiation sensor including an ionized layer and two electrodes arranged with the ionized layer interposed between the electrodes is referred to as an ionization chamber. The sensor section 203 in the present embodiment has a structure with the ionization chamber formed in layers in the depth direction.

The ionization chamber can be replaced by a semiconductor detector or a scintillation counter. This means that the sensor section 203, even if constructed to include a semiconductor detector or scintillation counter in multiple layers in the depth direction, yields substantially the same advantageous effects as those of the present embodiment. The two devices output an electrical signal in response to an energy loss of radiation that has occurred inside the device. In general, semiconductor detectors are semiconductor devices with a combination of a p-type semiconductor and an n-type semiconductor joined together. When a semiconductor device is to be used as a radiation sensor, a reverse bias is applied to the device to spread a depletion layer of a junction. The depletion layer exhibits a role as an ionized layer, and upon incidence of radiation, generates a number of holes/electron pairs that is proportional to an energy loss of the radiation. The holes/electron pairs drift according to a particular direction of an electric field within the depletion layer, and as is the case with ionization chambers, outputs an electric charge signal from electrodes connected to the p-type and n-type semiconductors, to the signal-processing unit 205.

The scintillation counter is a radiation sensor constituted by a scintillator such as a NaI crystal, GSO crystal, or organic EL, and a photodetector such as a photomultiplier tube. The scintillator exhibits a role as an ionized layer, and upon incidence of radiation, emits an amount of fluorescent light that is proportional to an energy loss of the radiation. The photodetector generates an electric charge proportional to the amount of light that has been emitted, and outputs an appropriate signal to the signal-processing unit 205.

Next, a method of calibrating the radiation detector 101 used for the particle therapy system according to the present embodiment, is described below using FIGS. 6A, 6B, and 2.

Figure 6A:
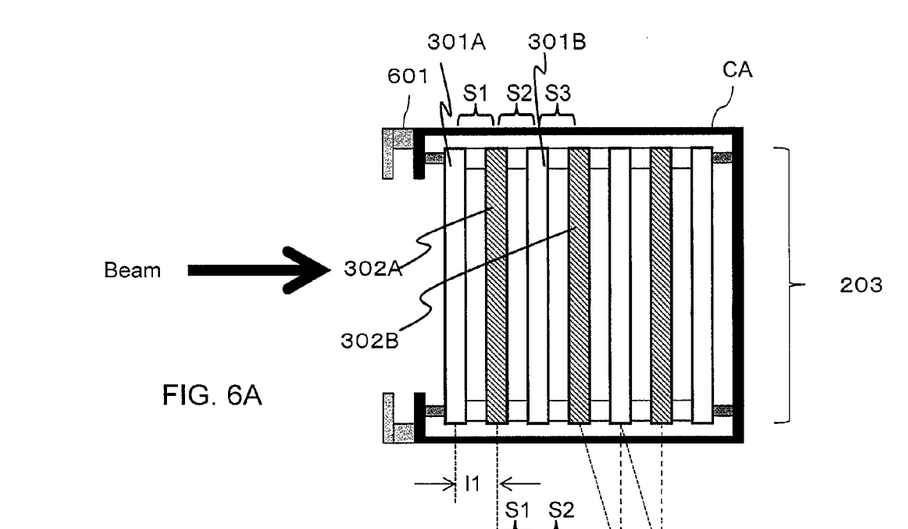
FIGS. 6A and 6B are explanatory diagrams of an exemplary method for calibrating the radiation detector according to the embodiment of the present invention.
Figure 6B:
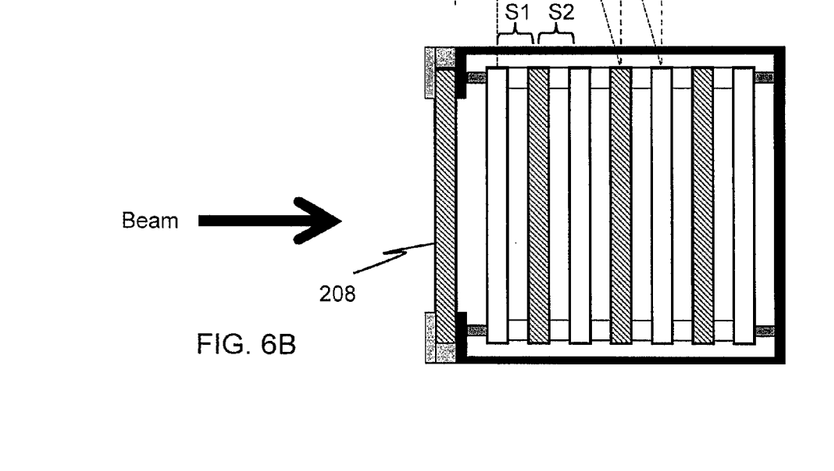

FIGS. 6A and 6B are explanatory diagrams of an exemplary method for calibrating the radiation detector used for the particle therapy system according to the embodiment of the present invention.

For the calibration of the radiation detector 101, a first measurement shown in FIG. 6A, and a second measurement shown in FIG. 6B are conducted. In the example of FIG. 6A, four printed circuit boards for electric-charge collection, namely 301A, 301B, etc., and three printed circuit boards for high-voltage application, namely 302A, 302B, etc., are arranged in layers at alternate positions in the sensor section 203. A first sensor S1 corresponds to a space constituted by a right half of a first printed circuit board 301A, a left half of a first printed circuit board 302A, and an ionized layer existing between the left and right halves of the two boards. In addition, a second sensor S2 corresponds to a space constituted by a right half of the first printed circuit board 302A, a left half of a second printed circuit board 301B, and an ionized layer existing between the left and right halves of the two boards. Furthermore, a third sensor S3 corresponds to a space constituted by a right half of the second printed circuit board 301B, a left half of a second printed circuit board 302B, and an ionized layer existing between the left and right halves of the two boards. Thickness 11 of one sensor is 4.0 mm on the average.

First, the first measurement shown in FIG. 6A is conducted. The radiation detector 101 is fixed to an upper surface of the patient couch 114 in an irradiation room (not shown) of the proton beam irradiation system 102. Next, the main control device 206 shown in FIG. 2 sends a control signal to the couch driving control device 116, the device of which then moves the patient couch 114 and positions the radiation detector 101 with a patient-positioning laser marker as a reference. In the present embodiment, the radiation detector is positioned so that the beam axis passes through central portions of the small electrodes 401 of each layer in the sensor section 203. Dedicated movable jigs for positioning the radiation detector 101 may be fabricated and these jigs may be used instead of the patient couch.

After positioning, measurement control of the radiation detector 101 and beam irradiation control of the proton beam irradiation system 102 are performed in a control room using the main control device 206. The main control device 206 first powers on the range shifter driving control device 202, the high-voltage power supply 204, and the signal-processing unit 205. This applies a high voltage to the high-voltage application electrode 501 of the printed circuit board 302 for high-voltage application, thus generating an electric field in the depth direction of the ionized layer. In the present embodiment, a high voltage of negative polarity for a grounding voltage of 0 V is applied to the high-voltage application electrode 501. All energy absorbers 201A of the range shifter 201 then stand by in a state offset from the passing position of the beam.

An operator sets a beam energy level, spot positions to be irradiated, the number of spots to be irradiated, and other necessary irradiation parameters, in the proton beam irradiation system 102, from the main control device 206, and then gives an instruction to start beam irradiation. Upon receiving the instruction to start the beam irradiation, the proton beam irradiation system 102 transmits an irradiation-starting signal to the main control device 206. Upon receiving the irradiation-starting signal, the main control device 206 transmits a measurement-starting signal to the signal-processing unit 205. The signal-processing unit 205, upon receiving the measurement-starting signal, starts integrating electric charges that have been input to the unit 205 itself. Immediately after the integration, the beam that has been accelerated in the synchrotron 108 is extracted into the rotating irradiation system 105 through the proton beam transfer 104, and the radiation detector 101 is irradiated with the beam in accordance with the parameters that the operator has set from the main control device 206.

A passage of the beam through the ionized layer generates a number of ion pairs, each pair being formed from a positive ion and an ionization electron, that is proportional to a dose of the beam in the ionized layer. The generated ion pairs drift in parallel to a direction of the electric field. Since the radiation detector 101 is positioned beforehand so that the beam axis passes through the centers of the small electrodes 401 of each layer, ionization electrons that were generated at positions that a distance from the beam axis is less than a radius of each small electrode 401 reach the small electrode 401, and ionization electrons that were generated at positions that the distance from the beam axis is equal to or greater than the radius of the small electrode 401 and less than a radius of each large electrode 402 reach the large electrode 402. In proportion to the number of electrons which have reached the small electrode 401 or the large electrode 402, a charge is developed in each of the lead wires 404, 405, 404', 405' connected to the electrodes 401, 402. The signal-processing unit 205 independently integrates each charge that has been input during the beam irradiation. The charges integrated are those which have been developed in the lead wires 404, 404' connected to the small electrode 401 of the printed circuit board 301 for electric-charge collection, and the charges that have been developed in the lead wires 405, 405' connected to the large electrode 402. Additionally, the signal-processing unit 205 integrates the ionization charges that have been output from the dose monitor 112.

Upon completion of the beam irradiation based on the operator-set parameters, the proton beam irradiation system 102 transmits an irradiation completion signal to the main control device 206. The main control device 206, upon receiving the irradiation completion signal, transmits a measurement completion signal to the signal-processing unit 205. Upon receiving the measurement completion signal, the signal-processing unit 205 stops the integration of the charges and after digitizing the integrated value of the charges which were obtained from the small electrodes and large electrodes of each layer of the sensor section 203, it transmits the digitized value as a first measurement result to the main control device 206. The signal-processing unit 205 also digitizes the integrated value of the charges which were obtained from the dose monitor 112, and transmits the digitized value to the main control device 206. The main control device 206 records the received integrated values. Additionally, the main control device 206 standardizes the integrated value that was obtained from the sensor section 203, by using the integrated value that was obtained from the dose monitor, and records a result of the standardization. After recording, the signal-processing unit 205 resets all integrated values that have been recorded in the unit 205 itself. This completes a sequence of the first measurement.

Next, the second measurement shown in FIG. 6B is conducted. The dummy absorber driving control device 209 places the dummy absorber 208 between fixing jigs 601 fitted in the sensor section 203 upstream of the traveling direction of the beam as viewed from the sensor section 203, and fixes the dummy absorber 208 to the fixing jigs 601. In other words, the dummy absorber 208 is placed in an anterior position in the direction of the measurement with the sensor section 203 and on the line where the beam propagates. Use of the fixing jigs 601 facilitates the placement of the dummy absorber 208 and leads to reduction in a time required for calibration. The present embodiment uses a spare printed circuit board 302 as the dummy absorber 208. Water-equivalent thickness of the dummy absorber 208 is therefore about 4.0 mm. The main control device 206 sends a control signal to the couch driving control device 116. The couch driving control device 116 then uses the patient couch 114 to move the sensor section 203 through a distance equivalent to one sensor's average thickness 11 (in the present example, 4.0 mm), in the traveling direction of the beam. The couch driving control device 116 moves the sensor section 203 in the traveling direction of the beam so that as shown in FIG. 6B, the first sensor S1 is placed in a position that the second sensor S2 has taken up in the traveling direction of the beam during the first measurement shown in FIG. 6A. That is to say, the sensor section 203 is moved through a distance of 4.0 mm in the traveling direction of the beam. The sensor section 203 is moved for the following reason. That is to say, a change in physical measuring position makes particle density of the beam lower with increasing distance from the radiation source, and hence, even when proton beams of the same energy are applied, the doses measured will change.

After the movement of the sensor section 203 using the patient couch, the operator sets irradiation parameters for the proton beam irradiation system 102 to the same values as those of the first measurement, and instructs the main control device 206 to start beam irradiation. The signal-processing unit 205 starts integration of charges and the proton beam irradiation system 102 irradiates the radiation detector 101 with a beam in accordance with the operator-set parameters.

Upon completion of the beam irradiation and then receipt of a measurement completion signal, the signal-processing unit 205 stops the integration of the charges and after digitizing an integrated value of the charges which have been obtained from the small electrodes and large electrodes of each layer of the sensor section 203, it transmits the digitized value as a second measurement result to the main control device 206. The signal-processing unit 205 also digitizes an integrated value of the charges which have been obtained from the dose monitor 112, and transmits the digitized value to the main control device 206. The main control device 206 records the received integrated values. Additionally, the main control device 206 standardizes the integrated value that was obtained from the sensor section 203, by using the integrated value that was obtained from the dose monitor 112, and records a result of the standardization. After recording, the signal-processing unit 205 resets all integrated values that have been recorded in the unit 205 itself. This completes a sequence of the second measurement.

The following sets forth a procedure for acquiring sensor-specific calibration coefficients using the measurement results that have been obtained during the first measurement and the second measurement.

Suppose that the integrated charge value that was obtained, during the first measurement not using the dummy absorber 208, from the small electrode 401 facing an i-th ionized layer (hereinafter, referred to as the ionized layer "i") as counted from an upper surface of the sensor section 203, is expressed as Qs(i). Also, suppose that the integrated charge value that was obtained from the large electrode 402 is expressed as Ql(i).

In addition, suppose that the integrated charge value that was obtained, during the second measurement using the dummy absorber 208, from the small electrode 401 facing the ionized layer "i", is expressed as qs(i). Furthermore, suppose that the integrated charge value that was obtained from the large electrode 402 is expressed as ql(i). The main control device 206 has already standardized these values with the integrated value of the dose extracted during the acquisition of the first and second measurement results, the integrated value of the extracted dose having been obtained from the dose monitor 112. Given an ideal radiation detector 101 free of variations in measurement results between the ionized layers, the integrated values satisfy following expressions (1) and (2):

$$Qs(i+1) = qs(i) \quad (1)$$

$$Ql(i+1) = ql(i) \quad (2)$$

Therefore, if a calibration coefficient for the integrated charge value obtained from the small electrode 401 facing the ionized layer "i" is taken as Cs(i), and a calibration coefficient for the integrated charge value obtained from the large electrode 402 is taken as Cl(i), the integrated charge values that were obtained in the radiation detector 101 of the present embodiment satisfy following expressions (3) and (4):

$$Cs(i+1) \times Qs(i+1) = Cs(i) \times qs(i) \quad (3)$$

$$Cl(i+1) \times Ql(i+1) = Cl(i) \times ql(i) \quad (4)$$

Putting these expressions in different forms allows one to get Cs(i+1) and Cl(i+1) shown in following expressions (5) and (6):

$$Cs(i+1) = Cs(i) \times qs(i) / Qs(i+1) \quad (5)$$

$$Cl(i+1) = Cl(i) \times ql(i) / Ql(i+1) \quad (6)$$

Additionally, solving above recurrence relations (5) and (6), with Cs(1)=Cl(1)=1, yields following expressions (7) and (8):

$$Cs(i) = qs(i-1) \times qs(i) \times \ldots \times qs(2) \times qs(1) / (Qs(i) \times Qs(i-1) \times \ldots \times Qs(3) \times Qs(2)) \ (i>1) \quad (7)$$

$$Cl(i) = ql(i-1) \times ql(i) \times \ldots \times ql(2) \times ql(1) / (Ql(i) \times Ql(i-1) \times \ldots \times Ql(3) \times Ql(2)) \ (i>1) \quad (8)$$

Finally, standardizing expressions (7) and (8) using average values Csa and Cla, each from i=1 to i=N, yields true calibration coefficients Cs'(i) and Cl'(i) as expressions (9) and (10), in which the average values Csa and Cla are denoted by expressions (11) and (12).

$$Cs'(i) = Cs(i)/Csa \quad (9)$$

$$Cl'(i) = Cl(i)/Cla \quad (10)$$

$$Csa = \Sigma Cs(i)/N \quad (11)$$

$$Cla = \Sigma Cl(i)/N \quad (12)$$

where N denotes the total number of ionized layers, this number being 6 in the examples of FIGS. 6A and 6B. Since it is presupposed that Cs(1)=Cl(1)=1, a ratio of expressions (7) and (8) is inaccurate. The calibration coefficients, however, vary in proportional to variations in ionized layer thickness and variations in gain of the signal-processing unit between the ionized layers, so if the small electrodes 401 and large electrodes 402 of each layer share the ionized layers and are connected to the same signal-processing unit 205, the average values of Cs(i) and Cl(i) are considered to agree. The corrected calibration coefficients are therefore obtained by the standardization with the average values. After being acquired, the calibration coefficients are recorded in the main control device 206.

In the present embodiment, a spare printed circuit board 302 for high-voltage application has been used as the dummy absorber 208. Provided, however, that the water-equivalent thickness of the dummy absorber 208 is nearly in agreement with the average water-equivalent thickness of 4.0 mm of each sensor, substantially the same advantageous effects as in the present embodiment can likewise be obtained by using any kind of dummy absorber 208. The dummy absorber 208 will therefore be replaced by any one of the sensors themselves that constitute the sensor section 203. For example, assume that the radiation detector 101 includes a semiconductor detector formed with a stacked sensor section 203. In this case, substantially the same advantageous effects as in the present embodiment can likewise be obtained even if a semiconductor detector absent in the sensor section 203 is used as a dummy absorber 208 for a purpose such as usage as a spare. Using an ionization chamber or a scintillation counter in place of the semiconductor detector likewise produces substantially the same effects.

While it has been described above that the dummy absorber 208 is driven by the dummy absorber driving control device 209, the dummy absorber 208 can likewise be driven by using the range shifter driving control device 202. Using the device 202 eliminates a need to provide the dummy absorber driving control device 209 separately, and substantially the same effects as in the embodiment described above can be obtained, even if the number of devices required for the calibration is reduced.

In addition, an operational effect equivalent to that of the dummy absorber 208 can likewise be realized by using the range shifter 201. For example, if an object with a water-equivalent thickness of 4.0 mm is required as the dummy absorber 208, an effect equivalent to inserting the dummy absorber 208 can be obtained by inserting energy absorbers 201A with water-equivalent thicknesses of 0.8 mm and 3.2 mm into the beam. Since combining energy absorbers 201A allows the range shifter to create a plurality of water-equivalent thicknesses, even if the radiation detector includes stacked sensors whose water-equivalent thicknesses differ from those used in the present embodiment, substantially the same effects as in the embodiment can be obtained without providing a dedicated dummy absorber 208.

Furthermore, the first measurement and the second measurement may be conducted in reverse order. In this case, first after setup of the dummy absorber 208 in place, irradiation with a proton beam is performed and a first measurement result is acquired using the radiation detector 101. Next, the dummy absorber 208 is removed from the proton beam irradiation axis and after the main control device 206 has sent a control signal to the couch driving control device 116, the driving control device 116 uses the patient couch 114 to move the sensor section 203 through a distance equivalent to the average thickness 11 (in the present example, 4.0 mm) of one sensor, to a position on a side opposite to the traveling direction of the beam, that is, towards the proton beam irradiation system 102. After this movement, proton beam irradiation using the same parameters as those of the above irradiation is executed and a measurement is conducted to acquire a second measurement result. Calibration coefficients can be obtained by conducting calculations for the obtained measurement results per expressions 1 to 12.

Figure 7:
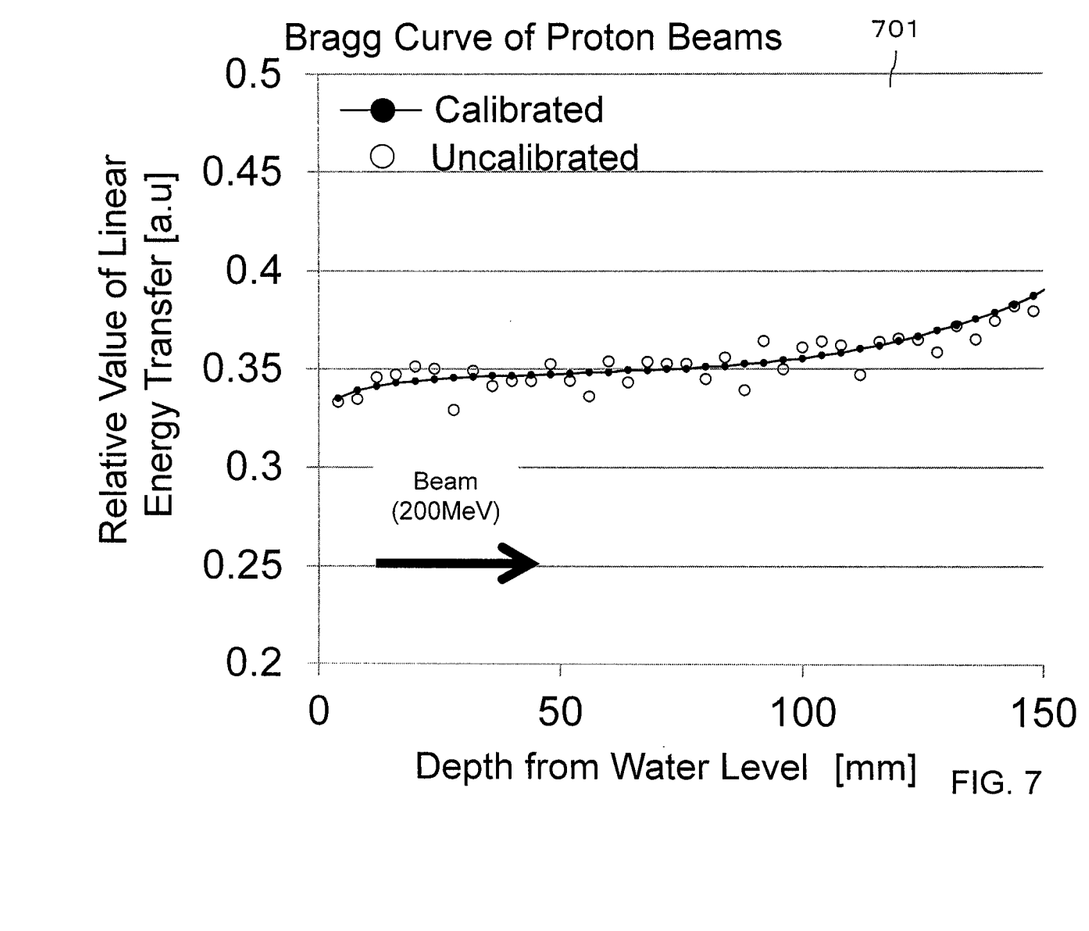
FIG. 7 is an explanatory diagram of calibration results on the radiation detector according to the embodiment of the present invention.

FIG. 7 is an explanatory diagram of calibration results on the radiation detector 101 used for the particle beam therapy system according to the embodiment of the present invention. Calibration results on the radiation detector 101 used for the particle beam therapy system according to the present embodiment are described below using FIG. 7.

FIG. 7 shows measurement results on a distribution (Bragg curve) of linear energy transfer which proton beams with an energy of 200 MeV form in the depth direction, the measurements having been conducted using the radiation detector 101 shown in FIG. 2.

A horizontal axis in FIG. 7 denotes depth from a water level, and a vertical axis denotes a relative value of the linear energy transfer. Results that were obtained without calibration are also shown for comparison. A white circle denotes uncalibrated sensor state and a black circle denotes a calibrated sensor state.

In the present embodiment, variations in sensor-specific data measurements are corrected and a smooth distribution is obtained.

In this way, in accordance with the present embodiment, a radiation detector with at least two sensors constructed in layers in the traveling direction of radiation can correct variations in output of each sensor easily and within a short time, without using a water-phantom dose detector. As a result, a burden upon the operator is relieved and a time required for adjustment and quality assurance of a particle beam therapy system is reduced.

Next, a procedure for measuring proton beam Bragg curve data using the radiation detector 101 of the present embodiment is set forth below. First, the radiation detector 101 is fixed to the upper surface of the patient couch 114 in the irradiation room of the proton beam irradiation system 102. Next, the patient couch 114 is moved and the radiation detector 101 is positioned with the patient-positioning laser marker as a reference. In the present embodiment, the radiation detector is positioned so that the beam axis passes through the centers of the small electrodes 401 of each layer in the sensor section 203. After positioning, the operator powers on the range shifter driving control device 202, the high-voltage power supply 204, and the signal-processing unit 205, through the main control device 206. All energy absorbers 201A of the range shifter 201 stand by in the state offset from the passing position of the beam.

The operator next sets a desired measuring spatial interval in the main control device 206. In the present embodiment, the measuring spatial interval is set to be a relatively large value of 1.0 mm envisaging a Bragg curve data measurement under a high incident-beam energy level at which a thick Bragg peak can be obtained. The operator further sets a beam energy level, spot positions to be irradiated, the number of spots to be irradiated, and other necessary irradiation parameters, in the proton beam irradiation system 102, from the main control device 206, and then gives an instruction to start beam irradiation. The signal-processing unit 205 starts integrating electric charges, and the proton beam irradiation system 102 irradiates the radiation detector 101 with the beam in accordance with the parameters that the operator has set in the main control device 206. In the Bragg curve measurement, since spots on the beam axis are irradiated with the beam, scanning magnets equipped in the irradiation nozzle 110 are not excited.

Upon completion of the beam irradiation and then receipt of a measurement completion signal, the signal-processing unit 205 stops the integration of the charges and after digitizing an integrated value of the charges which have been obtained from the small electrodes and large electrodes of each layer of the sensor section 203, it transmits the digitized value to the main control device 206. The signal-processing unit 205 also digitizes an integrated value of the charges which have been obtained from the dose monitor 112, and transmits the digitized value to the main control device 206. The main control device 206 records the received integrated values. Additionally, the main control device 206 standardizes the integrated value that was obtained from the sensor section 203, by using the integrated value that was obtained from the dose monitor 112, and records a result of the standardization. After recording, the signal-processing unit 205 resets all integrated values that have been recorded in the unit 205 itself.

Next, the main control device 206 instructs the range shifter driving control device 202 to insert energy absorbers 201A. In the present embodiment, the energy absorbers 201A of 0.2 mm and 0.8 mm in water-equivalent thickness are first inserted. After the insertion of the energy absorbers 201A, the main control device 206 once again instructs the proton beam irradiation system 102 to emit a beam in accordance with the parameters first specified by the operator. The signal-processing unit 205 starts integrating electric charges, and the proton beam irradiation system 102 irradiates the radiation detector 101 with the beam. Upon completion of the beam irradiation and then receipt of a measurement signal, the signal-processing unit 205 stops the integration of the charges and after digitizing an integrated value of the charges which have been obtained from the small electrodes and large electrodes of each layer of the sensor section 203, transmits the digitized value to the main control device 206. The signal-processing unit 205 also digitizes an integrated value of the charges which have been obtained from the dose monitor 112, and transmits the digitized value to the main control device 206. The main control device 206 records the received integrated values. Additionally, the main control device 206 standardizes the integrated value that has been obtained from the sensor section 203, by using the integrated value that has been obtained from the dose monitor 112, and records a result of the standardization. After recording, the signal-processing unit 205 resets all integrated values that have been recorded in the unit 205 itself.

Additionally, the main control device 206 instructs the range shifter driving control device 202 to insert the energy absorbers 201A of 0.4 mm and 1.6 mm in water-equivalent thickness. The energy absorbers 201A of 0.2 mm and 0.8 mm in water-equivalent thickness are instead unloaded from the passing position of the beam. After the insertion and unloading of the energy absorbers 201A, the main control device 206 once again instructs the proton beam irradiation system 102 to emit a beam in accordance with the parameters first specified by the operator. Measurement of Bragg curve data at the measuring spatial interval of 1.0 mm is repeated so that a total water-equivalent thickness of the energy absorbers 201A which have been loaded onto the beam axis becomes 0.0 mm (a state in which the energy absorbers 201A are all unloaded from the passing position of the beam), 1.0 mm, 2.0 mm, and 3.0 mm. By operating the range shifter in this way, the operator can measure Bragg curve data in increments of 1 mm using the radiation detector 101 of the present embodiment that has sensors pitched at 4 mm.

Suppose that the integrated charge value obtained from the small electrode 401 facing the ionized layer "i" when the total water-equivalent thickness of the loaded energy absorbers 201A is "r" is expressed as $Qs(i, r)$. Also, suppose that the integrated charge value obtained from the large electrode 402 is expressed as $Ql(i, r)$. These values are standardized by the main control device 206 with the integrated value that was obtained from the dose monitor 112. These values are also corrected by the main control device 206 on the basis of recorded calibration coefficients Cs' (i) and Cl' (i). Upon completion of all measurements, the main control device 206 adds Qs(i, r) and Ql(i, r), thus acquiring Q(i, r). That is to say, Q(i, r)=Qs(i, r)+Ql(i, r). The water-equivalent thicknesses of the printed circuit board 301 for electric-charge collection, the printed circuit board 302 for high-voltage application, and the ionized layer are already measured in advance by the operator and registered in the main control device 206. On the basis of this registered information, the main control device 206 converts Q(i, r) into Q(x), where "x" is the depth from the water level. The main control device 206 further multiplies Q(x) by a conversion coefficient to convert Q(x) into a dose D(x) in water. The conversion coefficient is registered in the main control device 206 in advance by the operator.

The electrodes that the small electrode 401 and the large electrode 402 constitute capture substantially all beams of the scanning method that have spread out laterally in a two-dimensional Gaussian distribution form. Therefore, the number of particles, "n", in one beam entering the ionized layer in contact with the small electrode 401 and the large electrode 402, can be regarded as constant, irrespective of the depth "x" from the water level. The main control device 206 converts D(x) into LET(x) on the basis of D(x)=LET(x)×n/S/p, where S is an area of the electrodes which the small electrode 401 and the large electrode 402 constitute. The main control device 206 displays a distribution of LET(x), or a Bragg curve, relative to "x", on a display (not shown). The operator confirms/analyses the Bragg curve displayed on the display, and evaluates adjustment results and performance of the proton beam irradiation system 102. The operator determines an approximate value of "n" from a charge stored within the accelerator, and records/registers the value of "n" in the main control device 206. If this value is not registered, the relative distribution of LET(x) is displayed on the display.

The radiation detector 101 of the present embodiment can also be used to measure a distribution of depth doses during volumetric irradiation. The volumetric irradiation means forming a uniform dose distribution in any region, called a target, of the subject being examined.

During the volumetric irradiation, the proton beam irradiation system 102 stops the irradiation once a predetermined dose has been delivered to one spot, and after that, it scans a next spot with the same beam. Scanning magnets equipped in the irradiation nozzle 110 are used when the beam is to be scanned in the lateral direction. After the predetermined dose has been delivered to a certain depth in all spots, the beam is scanned in the depth direction. The beam scan in the depth direction is implemented by changing the energy level of the beam using the range shifter (not shown) mounted in the synchrotron 108, the irradiation nozzle 110, or the like. Finally, a uniform dose is administered to all spots.

When the radiation detector 101 of the present embodiment is used to measure the distribution of depth doses during the volumetric irradiation, the steps required of setting the measuring spatial interval and measuring data at the set measuring spatial interval are substantially the same as for Bragg curve data measurement. Volumetric irradiation dose measurement, however, differs from Bragg curve data measurement in that only Qs is output from the small electrode 401.

Suppose that when the range shifter equipped in the radiation detector 101 is operated and the total water-equivalent thickness of the loaded energy absorbers 201A is "r", the integrated charge value obtained from the small electrode 401 facing the ionized layer "i" is expressed as Qs(i, r). These values are standardized by the main control device 206 with the integrated value that was obtained from the dose monitor. These values are also corrected by the main control device 206 on the basis of a recorded calibration coefficient Cs' (i). Upon completion of all measurements, the main control device 206 converts Qs(i, r) into Qs(x), where "x" is the depth from the water level. The water-equivalent thicknesses of the printed circuit board 301 for electric-charge collection, the printed circuit board 302 for high-voltage application, and the ionized layer are already measured in advance by the operator and registered in the main control device 206. On the basis of this registered information, the main control device 206 converts Qs(i, r) into Qs(x). The main control device 206 further multiplies Qs(x) by a conversion coefficient to convert Qs(x) into a dose D(x) in water, and displays relative data with respect to "x", on the display. The conversion coefficient is registered in the main control device 206 in advance by the operator. If the electrode 401 has small enough an area relative to a lateral irradiation range, the dose obtained during the measurement will be equivalent to a local dose at the center of the small electrode 401 in the radiation detector 101. A depth dose distribution can be output to the display. The operator can confirm/analyze the displayed results and evaluate adjustment results and performance of the proton beam irradiation system 102.

In addition, the radiation detector 101 of the present embodiment can form a depth dose distribution of a proton beam irradiation system employing a scattering method. In other words, the radiation detector 101 of the present embodiment can also be used to adjust, and evaluate the performance of, the proton beam irradiation system 102 that employs scattering irradiation.

A wobbling method, a typical example of scattering irradiation, is described below. A proton beam irradiation system using the wobbling method is substantially of the same construction as that of the proton beam irradiation system 102 using the scanning method, so the following description is given using FIG. 1. In the wobbling method, a scatterer, a collimator, a bolus, and a spread-out Bragg peak forming filter (not shown) are added to the passing position of the beam in the irradiation nozzle 110.

The wobbling method is used to form a laterally uniform dose distribution by circularly scanning a beam that has passed through the scatterer and spread out. Since the beam is circularly scanned in the lateral direction, a scanning magnet power supply (not shown) periodically reverses in polarity, shifts an electrical phase through 90 degrees between the scanning magnets, and supplies alternating currents equal in maximum current level, to the scanning magnets. The maximum current level determines a radius of the beam scanning path. The scanning magnet power supply determines a maximum supply current level from an incident energy level of the beam as well as from a size of the target that the operator has entered into the main control device 206. Additionally, the irradiation nozzle 110 determines thickness of the scatterer. The collimator changes the beam into an appropriate shape to fit a particular shape of the target, thereby reducing exposure of non-target regions to the beam. As a result, the irradiation dose is concentrated in the operator-set target region and a dose distribution as uniform as possible is formed in the lateral direction. A double-scattering method is also effective for forming the uniform dose distribution in the lateral direction. In the double-scattering method, two kinds of scatterers are arranged at the passing position of the beam, instead of the scanning magnets.

In the scattering method, a uniform dose distribution is formed in the depth direction using the spread-out Bragg peak forming filter. The proton beam irradiation system 102 controls the energy of the beam according to depth of the target that the operator has entered into the main control device 206, and matches the beam's reachable depth to the target region. The energy of the beam is changed by the range shifter (not shown) that is mounted in the synchrotron 108, the irradiation nozzle 110, or the like. In addition, the irradiation nozzle 110 places, at the passing position of the beam, the spread-out Bragg peak forming filter (hereinafter, referred to as SOBP filter) that is suitable for particular width of the target region in the depth direction and for the energy of the beam.

Functions of the SOBP filter are described below. The SOBP filter has stairway-shaped construction with different thickness, on a surface through which the beam passes. When the beam passes various steps of the SOBP filter in an appropriately allotted condition, an appropriately allotted energy distribution is given to the beam of single energy and thus a Bragg peak that the particle beam of the single energy forms in the depth direction is spread out to suit a particular shape of the target. A ridge filter or a range modulation wheel are useable as the SOBP filter.

In addition, in the scattering method, a bolus of a shape suited to the shape of the target is placed in the irradiation nozzle 110. The bolus controls the beam's reachable depth for each lateral position according to the shape of the target.

During the scattering irradiation represented by the wobbling method, using the radiation detector 101 in a manner similar to that of measuring the volumetric irradiation dose distribution described above allows depth dose distributions to be output to the display 208 and the operator to evaluate adjustment results and performance of the proton beam irradiation system 102.

As described above, in accordance with the present embodiment, the radiation detector with at least two sensors arranged in layers in the traveling direction of the beam can correct variations in sensor-specific output easily and within a short time, without using a water-phantom dose detector. As a result, the operator burden is relieved and the time required for the adjustment and quality assurance of a particle beam therapy system is reduced.

What is claimed is:

1. A radiation detector comprising:
   a sensor section having radiation sensors stacked on one another;
   a dummy absorber with a water-equivalent thickness equal to an average water-equivalent thickness of the stacked radiation sensors;
   a dummy absorber driving control section configured to place the dummy absorber at an anterior position in a direction of measurement by the sensor section, with the anterior position corresponding to a position at the line where radiation propagates;
   a sensor section driving control device configured to move the sensor section through a distance equal to average thickness of the stacked radiation sensors, at the line where the radiation propagates; and
   a signal-processing unit for calculating calibration coefficients for each radiation sensor, from measurement results output from the radiation detector when the dummy absorber is placed at the anterior position, measurement results output from the radiation detector when the dummy absorber is not placed at the anterior position, and an integrated extraction dose value of the radiation extracted during acquisition of the two sets of measurement results.

2. The radiation detector according to claim 1, wherein on a basis of whichever measurement results the signal-processing unit acquires earlier of the two sets of measurement results output from the radiation detector, one set being output when the dummy absorber is placed at the anterior position, and one set being output from the radiation detector when the dummy absorber is not placed at the anterior position, the sensor section driving control device determines a direction in which the sensor section is to be moved at the line where the radiation propagates, and the sensor section driving control device is configured to move the sensor section in the determined direction.

3. The radiation detector according to claim 2, wherein if the measurement results output from the radiation detector when the dummy absorber is placed at the anterior position are acquired earlier than the measurement results output from the radiation detector when the dummy absorber is not placed at the anterior position, the sensor section driving control device is configured to move the sensor section in a direction opposite to a traveling direction of the radiation, at the line where the radiation propagates.

4. The radiation detector according to claim 2, wherein if the measurement results output from the radiation detector when the dummy absorber is not placed at the anterior position are acquired earlier than the measurement results output from the radiation detector when the dummy absorber is placed at the anterior position, the sensor section driving control device is configured to move the sensor section in a traveling direction of the radiation, at the line where the radiation propagates.

5. The radiation detector according to claim 2, wherein the dummy absorber is the same member as a radiation sensor of the radiation sensors.

6. The radiation detector according to claim 2, further comprising:
   fixing jigs for fixing the dummy absorber to the anterior position;
   wherein the fixing jigs are fitted in the radiation detector.

7. The radiation detector according to claim 2, further comprising:
   a range shifter; and
   a range shifter driving control device for driving the range shifter;
   wherein the dummy absorber driving control section is the range shifter driving control device; and
   wherein the range shifter driving control device drives the range shifter by controlling the dummy absorber to ensure that the range shifter has water-equivalent thickness equal to that of the dummy absorber.

8. The radiation detector according to claim 2, further comprising:
   a range shifter; and
   a range shifter driving control device for driving the range shifter;
   wherein the dummy absorber driving control section is the range shifter driving control device; and
   wherein the range shifter driving control device drives the dummy absorber in addition to the range shifter.

9. A particle therapy system with the radiation detector of claim 2, wherein
   the integrated extraction dose value is acquired by a dose monitor equipped on a particle beam irradiation apparatus of the particle therapy system.

10. A particle therapy system with the radiation detector of claim 2, further comprising:
    a couch; and
    a couch driving control device;

wherein the sensor section driving control device is the couch driving control device.

11. The radiation detector according to claim 1, wherein if the measurement results output from the radiation detector when the dummy absorber is placed at the anterior position are acquired earlier than the measurement results output from the radiation detector when the dummy absorber is not placed at the anterior position, the sensor section driving control device is configured to move the sensor section in a direction opposite to a traveling direction of the radiation, at the line where the radiation propagates.

12. The radiation detector according to claim 1, wherein if the measurement results output from the radiation detector when the dummy absorber is not placed at the anterior position are acquired earlier than the measurement results output from the radiation detector when the dummy absorber is placed at the anterior position, the sensor section driving control device is configured to move the sensor section in a traveling direction of the radiation, at the line where the radiation propagates.

13. The radiation detector according to claim 1, wherein the dummy absorber is the same member as a radiation sensor of the radiation sensors.

14. The radiation detector according to claim 1, further comprising:
fixing jigs for fixing the dummy absorber to the anterior position;
wherein the fixing jigs are fitted in the radiation detector.

15. The radiation detector according to claim 1, further comprising:
a range shifter; and
a range shifter driving control device for driving the range shifter;
wherein the dummy absorber driving control section is the range shifter driving control device; and
wherein the range shifter driving control device drives the range shifter by controlling the dummy absorber to ensure that the range shifter has water-equivalent thickness equal to that of the dummy absorber.

16. The radiation detector according to claim 1, further comprising:
a range shifter; and
a range shifter driving control device for driving the range shifter;
wherein the dummy absorber driving control section is the range shifter driving control device; and
wherein the range shifter driving control device drives the dummy absorber in addition to the range shifter.

17. A particle therapy system with the radiation detector of claim 1, wherein
the integrated extraction dose value is acquired by a dose monitor equipped on a particle beam irradiation apparatus of the particle therapy system.

18. A particle therapy system with the radiation detector of claim 1, further comprising:
a couch; and
a couch driving control device;
wherein the sensor section driving control device is the couch driving control device.

19. A calibration method for a radiation detector including a sensor section having radiation sensors stacked one another, the method comprising:
acquiring a first measurement result by measuring radiation passing through the sensor section;
placing, at an anterior position in a direction of measurement by the sensor section, with the anterior position corresponding to a position at the line where the radiation propagates, a dummy absorber having water-equivalent thickness equal to average water-equivalent thickness of the stacked radiation sensors;
moving the sensor section through a distance equal to average thickness of the stacked radiation sensors, in a traveling direction of the radiation, at the line where the radiation propagates;
acquiring a second measurement result by measuring the radiation passing through the sensor section after passing through the absorber; and
calculating calibration coefficients for each of the radiation sensors, from the first measurement result, the second measurement result, and an integrated extraction dose of the radiation extracted during the acquisition of the first measurement result and the second measurement result.

20. A calibration method for a radiation detector including a sensor section having radiation sensors stacked one another, the method comprising:
placing, at an anterior position in a direction of measurement by the sensor section, with the anterior position corresponding to a position at the line where radiation propagates, a dummy absorber having water-equivalent thickness equal to average water-equivalent thickness of the stacked radiation sensors;
acquiring a first measurement result by measuring the radiation passing through the sensor section after passing through the absorber;
removing the dummy absorber from the line where the radiation propagates;
moving the sensor section through a distance equal to average thickness of the stacked radiation sensors, in a traveling direction of the radiation, at the line where the radiation propagates;
acquiring a second measurement result by measuring the radiation passing through the sensor section; and
calculating calibration coefficients for each of the radiation sensors, from the first measurement result, the second measurement result, and an integrated extraction dose of the radiation extracted during the acquisition of the first measurement result and the second measurement result.

* * * * *